United States Patent [19]
Archibald et al.

[11] 3,962,258
[45] June 8, 1976

[54] 1,2,3,4,6,7,12,12b-OCTAHYDRO-2-BEN-ZAMIDOINDOLO[2,3-a]QUINOLIZINE

[75] Inventors: John Leheup Archibald, Windsor; John Lambert Jackson, Henley-on-Thames; Brian John Bushell, Southampton, all of England

[73] Assignee: John Wyeth & Brother Limited, Taplow, England

[22] Filed: May 17, 1974

[21] Appl. No.: 470,765

[30] Foreign Application Priority Data
May 25, 1973 United Kingdom............... 25299/73

[52] U.S. Cl..................... 260/293.53; 260/293.61; 424/267
[51] Int. Cl.²....................................... C07D 401/06

[58] Field of Search............................... 260/293.53

[56] References Cited
UNITED STATES PATENTS

| | | | |
|---|---|---|---|
| 3,415,831 | 12/1968 | Weisbach............................ | 260/288 |
| 3,753,995 | 8/1973 | Martel et al. .................. | 260/293.53 |
| 3,850,936 | 11/1974 | Herbst et al. .................. | 260/293.53 |

*Primary Examiner*—G. Thomas Todd

[57] ABSTRACT

The invention provides indolo[2,3-a]quinolizine derivatives which are active as hypotensive and antihistamine agents. The invention also provides a pharmaceutical composition comprising an indolo[2,3-a]quinolizine derivative together with a pharmaceutical carrier.

1 Claim, No Drawings

1,2,3,4,6,7,12,12B-OCTAHYDRO-2-BENZAMIDOINDOLO[2,3-A]QUINOLIZINE

This invention relates to new indole derivatives, to processes for the preparation thereof, and to pharmaceutical compositions containing such derivatives.

More particularly the present invention provides a compound having the general formula

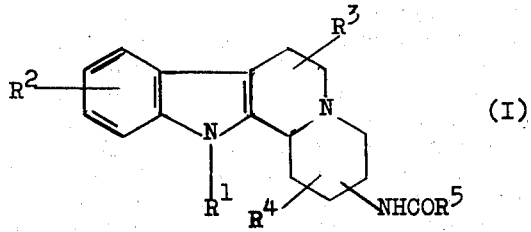

wherein $R^1$ represents hydrogen, lower alkyl, or benzyl; $R^2$ represents hydrogen, lower alkoxy, or hydroxy; $R^3$ represents hydrogen, hydroxy or an oxo group (i.e. =O) $R^4$ represents hydrogen or lower alkyl; and $R^5$ represents phenyl, benzyl, a cycloalkyl radical containing 5 to 7 carbon atoms, or phenyl substituted by halogen, lower alkyl or lower alkoxy; or a pharmaceutically acceptable acid addition or quaternary ammonium salt thereof.

The terms "lower alkyl" and "lower alkoxy" as used herein indicate that the alkyl and alkoxy radicals each contain from 1 to 4 carbon atoms.

Examples of the group $R^1$ are hydrogen, methyl, ethyl, n-propyl, isopropyl, n-butyl, isobutyl and benzyl. Preferably $R^1$ is hydrogen or methyl. Examples of $R^2$ are hydrogen, methoxy, ethoxy, hydroxy. Preferably $R^2$ is hydrogen. Examples of the group $R^3$ are hydrogen, hydroxy, oxo, (i.e. =O). Preferably $R^3$ is hydrogen. The group $R^4$ can be, for example, hydrogen, methyl, ethyl, or n-propyl. preferably $R^4$ is hydrogen. Examples of $R^5$ are phenyl; phenyl substituted by halogen (such as chlorine), by alkoxy (such as methoxy or ethoxy), by alkyl (such as methyl or ethyl); benzyl; or cyclohexyl.

Examples of the acid addition salts are the hydrochloride, hydrobromide and hydroiodide. Examples of the quaternary ammonium salts are those formed by addition of methyl bromide or methyl iodide.

The novel compounds provided by the present invention possess pharmacological properties and/or may be intermediates for the other compounds of this invention. In particular the novel compounds of this invention possess hypotensive activity and anti-histamine activity when tested on warm blooded animals.

For example, 1,2,3,4,6,7,12,12b-octahydro-2-benzamidoindolo[2,3-a]quinolizine hydrochloride showed hypotensive activity when administered intravenously to normotensive rats; and also anti-histamine activity when tested on guinea pig ileum by a method based on Burn, J. H., Practical Pharmacology, Blackwell, Oxford, 1952.

The novel compounds of general formula (I) may be prepared by a number of processes. A first general method of preparation comprises cyclising a compound of general formula:

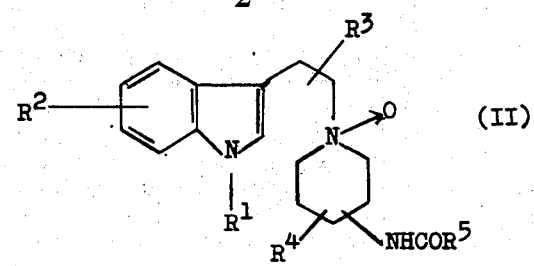

wherein $R^1$, $R^2$, $R^3$, $R^4$ and $R^5$ are as hereinbefore defined. The cyclisation of compounds of general formula (II) may be brought about in a number of ways. For example a compounds of formula (II) may be cyclised by heating in the presence of ferrous ions and a suitable acidic medium. Examples of suitable acidic media are methanol/acetic acid or sulphuric acid/pyridine. Examples of compounds giving ferrous ions are ferrous sulphate or ferrous chloride.

The compounds of formula (II) may be prepared by reacting compounds of formula

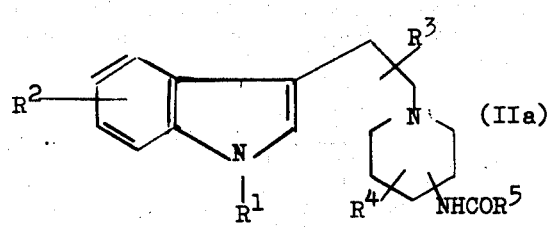

wherein $R^1$, $R^2$, $R^3$, $R^4$, $R^5$ and A have the meanings above, with a N-oxidising agent. Examples of N-oxidising agents are hydrogen peroxide and peroxy acids such as performic, peracetic, trifluoroperacetic, perbenzoic, substituted perbenzoic (e.g., m-chloro) and perphthalic acids. A preferred peroxyacid is m-chloroperbenzoic acid.

The reaction is generally carried out using an inert solvent, preferably dichloromethane or chloroform. A low reaction temperature, preferably from −10°C to +25°C, e.g., about 0°C, is used.

The starting materials for the above rection having general formula (IIa) are known compounds and methods for their preparation and the compounds themselves are described in U.K. Patent Specification Nos. 1,218,570 and 1,273,563, and in Irish Patent Application No. 152/72 laid open to public inspection on August 11th, 1972.

Alternatively cyclisation of compounds of general formula (II) to give compounds of general formula (I) may be accomplished by reaction with trifluoroacetic anhydride/H+ mixtures, e.g. a mixture of trifluoroacetic anhydride and trifluoroacetic acid.

A further process for preparing the novel compounds of this invention comprises reacting a compound of general formula:

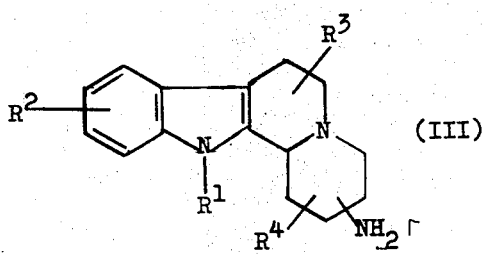

wherein $R^1$, $R^2$, $R^3$ and $R^4$ are as defined above, with a reactive derivative of an acid of general formula $R^5COOH$, wherein $R^5$ is as defined above. As a reactive derivative of the acid of formula $R^5COOH$ used in the process described above, it is preferable usually to use a halide (for example the chloride or bromide) or an anhydride. Other examples of reactive derivatives of the acid $R^5COOH$ which may be used are the acid azide, mixed anhydrides and active esters. Furthermore the compounds of formula (I) wherein $R^5$ is as defined in connection with formula $R^5COOH$ may also be prepared by treating a compound of formula (II) with the acid $R^5COOH$ in the presence of a known condensing agent (for example, a carbodiimide), or by first activating the amino function (for example, by forming the phosophazo derivatives and then reacting with the acid $R^5COOH$. In connection with the introduction of the $-COR^5$ group into a compound of formula (III); reference may be made to "Chemistry of the Amino Acids" by Greenstein and Winitz (John Wiley & Sons. Inc., Publishers, 1961) at pages 782–883 and 943–1108.

The compound of formula III, used as starting material in the process above, may be prepared by hydrolysing a corresponding acylamino compound of general formula:

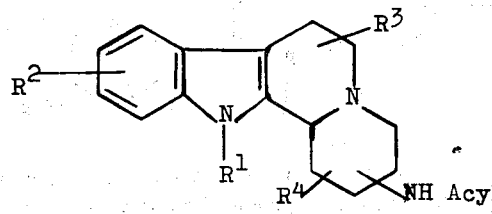 (IV)

wherein $R^1$, $R^2$, $R^3$ and $R^4$ are as defined above and "Acyl" represents an acyl radical, e.g. acetyl or benzoyl. The hydrolysis may be carried out using a mineral acid, such as hydrochloric acid.

When a compound of general formula (I) is prepared in which $R^1$ is hydrogen then that compound may be lower alkylated, or benzylated at the 12-position by mmethods known per se to give the others compounds of formula (I) in which $R^1$ represents lower alkyl, or benzyl. For example an alkali metal salt, e.g. the sodium salt may be prepared and reacted with a lower alkyl- or a benzyl-halide.

A further aspect of the invention is the provision of a pharmaceutical composition comprising a compound of general formula I, or a pharmaceutically acceptable acid addition or quaternary ammonium salt thereof, together with a pharmaceutical carrier. Any suitable carrier known in the art may be used to prepare the pharmaceutical compositions. In such a composition the carrier may be solid, liquid or a mixture of solid and liquid. In the solid form the compositions include powders, tablets and capsules. In the liquid or solid/liquid form the compositions include solutions, suspensions and creams.

When the compounds of this invention are employed as hypotensive agents they may be administered to warm blooded animals, e.g. mice, rats, rabbits, dogs, cats or monkeys alone or in combination with pharmaceutically acceptable carriers, the proportion of which is determined by the solubility and chemical nature of the compounds, chosen route of administration and standard biological practice. For example, they may be administered orally in the form containing such excipients for example starch, milk or sugar, e.g. as tablets or capsules. They may also be administered orally in the form of solutions or they may be injected as solutions. For intraperitoneal adminstration they may be used in the form of sterile solutions or suspensions containing other solutes for example enough saline or glucose to make the solution isotonic.

The dosage of the present compounds will vary with the mode of administration and the particular compound chosen. Furthermore, it will vary with the particular subject under treatment. Generally treatment is initiated with doses substantially less than the optimum dose of the compound. Thereafter, the dosage may be increased by small amounts until the optimum effect under the circumstances is reached. In general, the compounds of this invention are most desirably administered at a concentration level that will generally afford effective results without causing any harmful or deleterious side effects.

The following non-limiting examples illustrate the invention:

EXAMPLE 1

1,2,3,4,6,7,12,12b-Octahydro-2-benzamido-indolo[2,3-a]-quinolizine.

4-Benzamido-1-[2-(indol-3-yl)ethyl]piperidine-N-oxide (26.4 g., 0.10 mole) was suspended in methanol (4 liters) and ferrous sulphate heptahydrate (100 g), followed by glacial acetic acid (750 mls.), were added. The mixture was refluxed for 18 hours, allowed to cool, and $H_2S$ bubbled through for 10 minutes. Sodium borohydride (300 g.) was added portionwise, with stirring and cooling, and $H_2S$ was passed through for a further 30 minutes. After standing for 1 hour, the mixture was filtered (Kieselguhr); the filtrate was evaporated to dryness; then water (250 mls.) and 10N sodium hydroxide solution added until strongly basic. The alkaline solution was extracted thoroughly with benzene, and then the benzene was washed with water before drying ($M_gSO_4$). Evaporation afforded a mixture of the title compound and de-oxygenated starting material (7.70 g.) Chromatography, using a basic alumina column and gradient elution with benzene/ethyl acetate gave the pure title compound (1.16 g). Recrystallation from methanol/ether/HCl provided the hydrochloride hydrate as colourless needles, m.p. 276°.

Found: C, 68.44; H, 6.49; N, 10.61%. $C_{22}H_{23}N_3O.HCl.1/4.H_2O$ requires: C, 68.38; H, 6.39; N, 10.87%.

EXAMPLES 2 to 23

By procedures analogous to Example 1 the following compounds can be prepared:

1,2,3,4,6,7,12,12b-Octahydro-2-[4-chlorobenzamido]indolo[2,3-a]quinolizine.

1,2,3,4,6,7,12,12b-Octahydro-2-[3-chlorobenzamido]indolo[2,3-a]quinolizine.

1,2,3,4,6,7,12,12b-Octahydro-24-methoxybenzamido]indolo[2,3-a]quinolizine.

1,2,3,4,6,7,12,12b-Octahydro-2-[3-methoxybenzamido]indolo[2,3-a]quinolizine.

1,2,3,4,6,7,12,12b-Octahydro-22-methoxybenzamido]indolo-[2,3-a]quinolizine.

1,2,3,4,6,7,12,12b-Octahydro-2-[4-methylbenzamido]indolo[2,3a]quinolizine.

1,2,3,4,6,7,12,12b-Octahydro-2-[3-methylbenzamido]indolo-[2,3-a]quinolizine.

1,2,3,4,6,7,12,12b-Octahydro-2-[2-methylbenzamido]indolo-[2,3-a]quinolizine.

1,2,3,4,6,7,12,12b-Octahydro-2-phenylacetamido-indolo[2,3-a]quinolizine.

1,2,3,4,6,7,12,12b-Octahydro-2-benzamido-12-methyl-indolo-[2,3-a]quinolizine.

1,2,3,4,6,7,12,12b-Octahydro-2-[4-chlorobenzamido]-12-methyl-indolo[2,3-a]quinolizine.

1,2,3,4,6,7,12,12b-Octahydro-2-[4-methylbenzamido]-12-methyl-indolo[2,3-a]quinolizine.

1,2,3,4,6,7,12,12b-Octahydro-2-[4-methoxybenzamido]-12-methyl-indolo[2,3-a]quinolizine.

1,2,3,4,6,7,12,12b-Octahydro-2-benzamido-12-benzyl-indolo-[2,3-a]quinolizine.

1,2,3,4,6,7,12,12b-Octahydro-2-cyclohexanecarboxamidoindolo-[2,3-a]quinolizine.

1,2,3,4,6,7,12,12b-Octahydro-2-cyclopentanecarboxamidoindolo-[2,3-a]quinolizine.

1,2,3,4,6,7,12,12b-Octahydro-2-cycloheptanecarboxamidoindolo-[2,3-a]quinolizine.

1,2,3,4,6,7,12,12b-Octahydro-2-benzamido-7-hydroxy-indolo-[2,3-a]quinolizine.

1,2,3,4,6,7,12,12b-Octahydro-2-[4-methoxybenzamido]-7-hydroxy-indolo[2,3-a]quinolizine.

1,2,3,4,6,7,12,12b-Octahydro-2-benzamido-10-methoxy-indolo-[2,3-a]quinolizine.

1,2,3,4,6,7,12,12b-Octahydro-2-[4-chlorobenzamido]-10-methoxy-indolo[2,3-a]quinolizine.

1,2,3,4,6,7,12,12b-Octahydro-2-benzamido-7-oxo-indolo[2,3-a]quinolizine.

We claim:
1. 1,2,3,4,6,7,12,12b-octahydro-2-benzamido-indolo[2,3-a]quinolizine or a pharmaceutically acceptable acid addition or quaternary ammonium salt thereof.

* * * * *